(12) United States Patent
Mondro

(10) Patent No.: US 8,337,422 B2
(45) Date of Patent: Dec. 25, 2012

(54) DIAGNOSTIC TEST STRIP HAVING FLUID TRANSPORT FEATURES

(75) Inventor: Jason Mondro, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 538 days.

(21) Appl. No.: 12/502,585

(22) Filed: Jul. 14, 2009

(65) Prior Publication Data
US 2011/0015545 A1    Jan. 20, 2011

(51) Int. Cl.
*A61B 5/00* (2006.01)
*B65D 81/00* (2006.01)

(52) U.S. Cl. ......................... 600/583; 600/573

(58) Field of Classification Search ............. 600/583, 600/584
See application file for complete search history.

(56) References Cited

U.S. PATENT DOCUMENTS

| | | | |
|---|---|---|---|
| 5,407,554 A | 4/1995 | Saurer | 204/403 |
| 5,437,999 A | 8/1995 | Diebold et al. | |
| 5,741,634 A | 4/1998 | Nozoe et al. | 435/4 |
| 6,143,164 A | 11/2000 | Heller et al. | |
| 6,558,402 B1 | 5/2003 | Chelak et al. | |
| 6,878,345 B1 | 4/2005 | Astle | |
| 6,881,578 B2 | 4/2005 | Otake | 436/44 |
| 6,893,545 B2 | 5/2005 | Gotoh et al. | 204/403.04 |
| 7,192,405 B2 | 3/2007 | DeNuzzio et al. | 600/583 |
| 7,378,270 B2 | 5/2008 | Azarnia et al. | |
| 7,498,132 B2 | 3/2009 | Yu et al. | 435/6 |
| 7,731,900 B2 | 6/2010 | Haar et al. | |
| 2005/0036909 A1 * | 2/2005 | Erickson et al. | 422/61 |
| 2005/0245845 A1 * | 11/2005 | Roe et al. | 600/583 |
| 2007/0020143 A1 | 1/2007 | Seidenstricker et al. | |
| 2008/0103415 A1 * | 5/2008 | Roe et al. | 600/583 |
| 2011/0015546 A1 | 1/2011 | Mondro et al. | |
| 2011/0174637 A1 | 7/2011 | Mondro et al. | |

* cited by examiner

*Primary Examiner* — Jeffrey G Hoekstra
(74) *Attorney, Agent, or Firm* — Alan W. Fiedler; Fitzpatrick, Cella, Harper & Scinto

(57) ABSTRACT

A test strip for testing a blood sample is provided with a fluid transport feature to facilitate transport of a blood sample obtained from a lancing operation through a capillary channel to a measurement site. A fluid transport path is defined on the major face of the strip terminating at the mouth of the capillary channel. The fluid transport path includes a depending portion at one end opposite the mouth of the channel. The depending portion extends away from the strip on the side facing the fluid sample, such that a droplet of fluid sample contacting the depending portion is directed toward the mouth of the capillary channel. Thereafter the sample moves by capillary action to the measurement site.

16 Claims, 5 Drawing Sheets

DIAGNOSTIC TEST STRIP HAVING FLUID TRANSPORT FEATURES

BACKGROUND OF THE INVENTION

1. Field of the Invention

The invention is in the field of fluid sample acquisition and testing. In particular, the invention is directed to a test strip having features that facilitate transport of a blood sample obtained from a person's body to a measurement site on the strip.

2. Description of the Related Art

In the medical and diagnostic field, and particularly in the field of diabetes care, it is often desirable to perform testing on a fluid sample, such as a blood sample, collected on a test strip. The trend is to collect and test smaller fluid samples, including sub-microliter samples (i.e., samples having a volume of 1 µL or less). In this context, it is desirable to be able to direct a fluid sample collected on a test strip to a measurement site on the strip, and to ensure that enough of the sample is available to perform the required testing of the sample.

It would be desirable in this context to have means to direct the fluid sample to the measurement site, ensuring sufficient sample to perform a measurement, without requiring involvement by the user.

In application Ser. No. 12/502,594, filed concurrently herewith, a device has been proposed in which a strip having a bending portion is positioned opposite a fluid sample collected from a user's body. The bending motion leverages adherence and transport dynamics of the fluid sample on the strip to ensure that sufficient sample reaches the measurement site from a given minimum sample volume. It would be desirable in this context to have a strip that facilitates movement of a fluid droplet to the measurement site after the fluid has been contacted by a rolling bend portion of a strip to a measurement site on the strip.

SUMMARY OF THE INVENTION

In one aspect, the invention is a diagnostic test strip for testing a fluid sample, including for example, a blood sample obtained from a patient's body in a lancing operation. The strip has a first major side which is positioned facing a sample. A capillary channel having a mouth at one end and containing a measurement site toward the opposite end is positioned on the major side, such that fluid sample contacting the strip moves from the mouth through the capillary channel to the measurement site. The strip is provided with a fluid transport path which may be defined as having one end at the mouth of the capillary channel. A depending portion extends away from the strip on the side facing the fluid sample, such that a droplet of fluid sample contacting the depending portion is directed from the depending portion, along the fluid transport path, and to the mouth of the capillary channel.

In a preferred embodiment, the strip is provided with a lancet hole for passage of a lancet, and the fluid transport path extends from the side of the lancet hole adjacent the depending portion to the mouth of the capillary channel. The lancet passes through the hole to acquire blood from a patient, which is drawn with the lancet back through the lancet hole. The strip is arranged to a have a rolling bend in the portion of the strip that contacts the fluid sample, which causes a depending portion on the side of the lancet hole to extend in the direction of the fluid sample. This may be accomplished using slits extending from the sides of the hole, for example. The reduced width of the depending portion causes the droplet to be guided toward the longitudinal centerline of the strip and toward the mouth of the capillary channel.

DETAILED DESCRIPTION OF THE PREFERRED EMBODIMENTS

Figure 1:
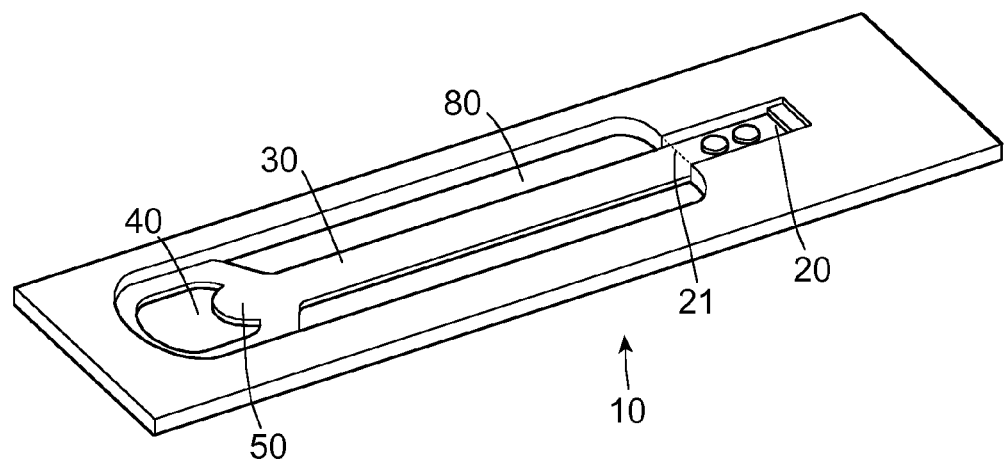
FIG. 1 depicts a test strip according to the invention.
Figure 2A:
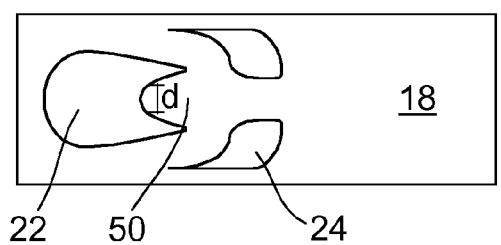
FIG. 2A, FIG. 2B, FIG. 2C and FIG. 2D depict layers that may be stacked to form a test strip laminate.
Figure 2B:
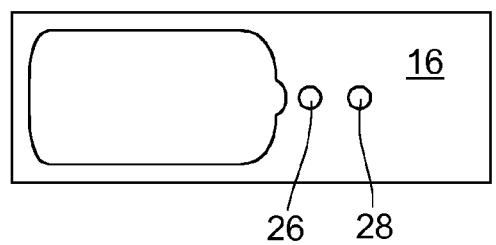
Figure 2C:
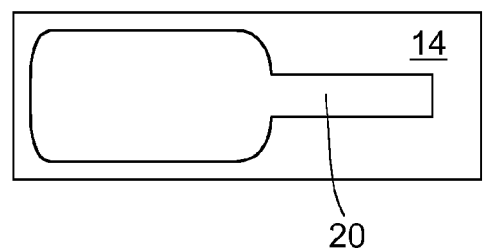
Figure 2D:
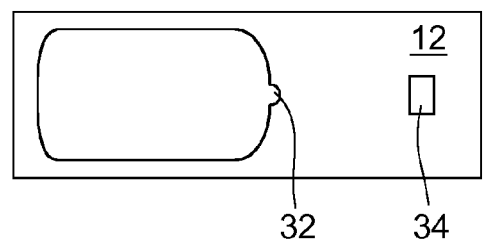

Referring to FIG. 1, test strip 10 is shown with the major side facing up. A top layer is removed to show the features of capillary channel 20. Fluid transport path 30 extends from the depending portion 50 to the mouth 21 of the capillary channel 20. In the embodiment shown, trenches 80 on opposite sides of the fluid transport path 30 are recessed. Surface tension and adhesion of the sample fluid to the fluid transport path 30 prevent sample fluid from flowing into the trenches 80.

Figure 3:
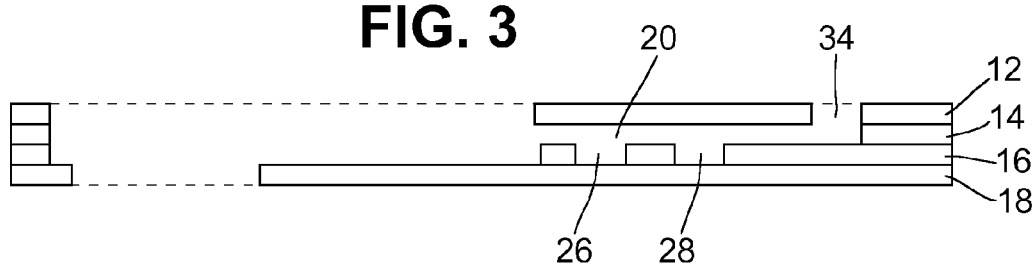
FIG. 3 shows a cross section of the stacked layers of FIG. 2A through FIG. 2D.

The strip may be a multilayer laminate made up of layers as shown in FIG. 2A, FIG. 2B, FIG. 2C and FIG. 2D, stacked to obtain a cross-sectional configuration such as shown in FIG. 3. Layers used to form a strip include layer 18 patterned with cutouts 22, 24 to form the depending portion 50; layer 16 defining reagent wells 26, 28 for electrochemical determination of blood glucose; layer 14, which defines the capillary channel walls, and top layer 12, which forms the top of the capillary channel including notch 32 at the mouth and vent 34 at the rear of the channel, which assist capillary flow of the sample. The design of the layers may be modified without departing from the scope of the invention. The construction of multilayer laminate test strips is described in U.S. Pat. Nos. 7,192,405 and 7,498,132, for example, incorporated herein by reference, and will not be further elaborated.

In the embodiment depicted in these Figures, lancet hole space 40, is provided for passage of a lancet. A fluid transport path 30 extends from the edge of lancet hole space 40 to the mouth of the capillary channel 20. In the embodiment shown, the capillary channel 20 comprises wells 26, 28, containing reagents for performance of a diagnostic test, such as a blood glucose measurement using an electrochemical reaction. However, any method of performing a diagnostic test may be used, and the invention is not limited to the use of electrochemical reagents to perform the diagnostic test.

The fluid transport path 30 is preferably constructed of a hydrophobic material, so that a fluid sample should form a contact angle with the fluid transport path of greater than at least about 50 degrees, preferably greater than about 60 degrees and most preferably greater than about 70 degrees. Materials such as Mylar® having the appropriate characteristics can be used as laminate materials. Alternatively, treatments can be performed to render a different material for the fluid transport path more hydrophobic, including without limitation, silane or Rainex® coatings.

The fluid transport path 30 is provided with a depending portion 50. When the strip initially contacts the fluid sample to be tested, the depending portion 50 preferentially contacts a droplet of fluid sample so that the droplet is directed to the center of the strip. The edges of the depending portion have reduced width d at the contact point which causes the droplet to be directed toward the center of the strip and toward the mouth of the capillary channel.

The length of the fluid transport path 30 may vary from about 2 mm to about 6 mm. The path length should be larger than the blood droplet diameter to allow detection of the drop before filling the capillary. As the length of the path increases, the chance for sample loss also increases requiring a larger initial sample.

In preferred embodiments, the fluid transport path 30 is raised with respect to an area or areas adjacent the strip. It is believed that a droplet contacting a narrower raised portion initially will tend to stay on that path as the fluid progresses toward the capillary channel. The edge of the raised area creates a sharp change in direction of the surface that the sample is in contact with, and surface tension and contact angle keep it from falling off. While not limiting of the invention, in the preferred embodiment shown in FIG. 1, recesses 80 adjacent the fluid transport path 30 extend on either side of the fluid transport path for substantially its entire length, from near the depending portion 50 to near the mouth of the capillary channel 20. Being narrower, the fluid transport path prevents loss of the sample along the strip.

Figure 4A:
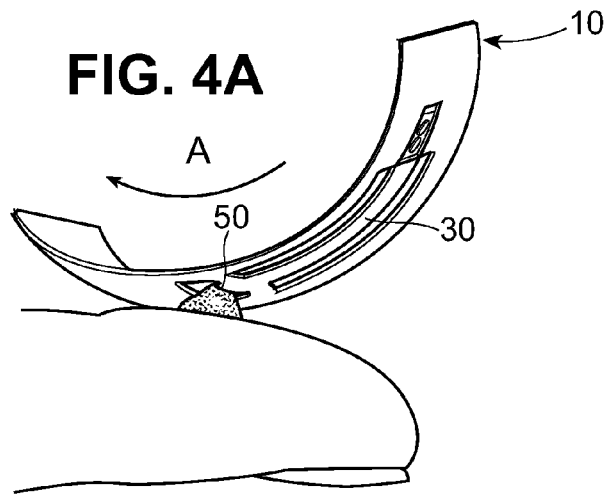
FIG. 4A, FIG. 4B, and FIG. 4C depict a test strip according to the invention in a bending state proximate a blood sample to be tested, at different stages during the procedure of contacting the sample.
Figure 4B:
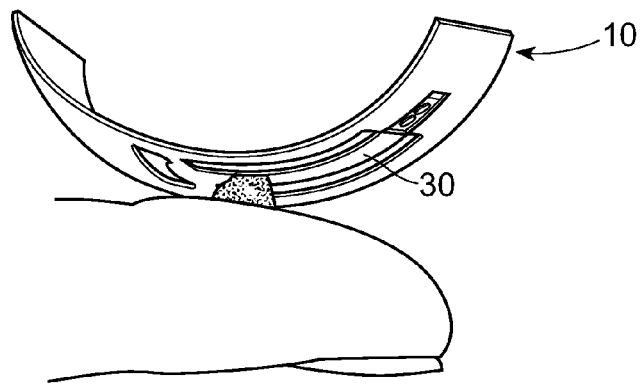
Figure 4C:
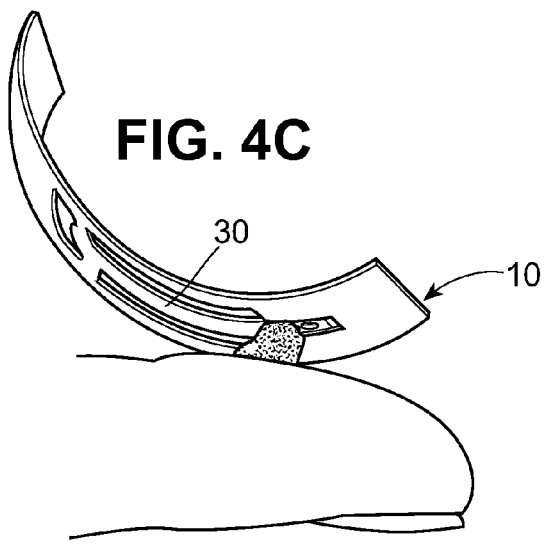

FIG. 4A, FIG. 4B and FIG. 4C depict a preferred embodiment in which a strip according to the invention is positioned proximate a fluid sample in a bending state, and moved so that a fluid sample (such as a blood droplet) is transported from the lancet hole space 40 on the fluid transport path 30 to the mouth of the capillary channel 20. The strip is moved in a rolling bend motion, in the direction shown by arrow. FIG. 4C represents a point in time shortly after FIG. 4B, which represents a point in time shortly after FIG. 4A. The bend in the strip causes the depending portion 50 to extend away from the strip toward the fluid sample. Preferably, the depending portion extends at least about 100 μm to contact the fluid sample, measured as a distance on a line perpendicular to a line tangent to the bend of the strip to the most extended point on the depending portion away from the surface of the strip.

Figure 5A:
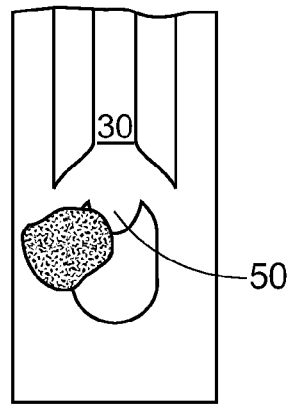
FIG. 5A, FIG. 5B, FIGS. 5C, and 5D depict the positioning of a fluid sample droplet on the test strip at different stages after a droplet of fluid sample is contacted with a test strip.
Figure 5B:
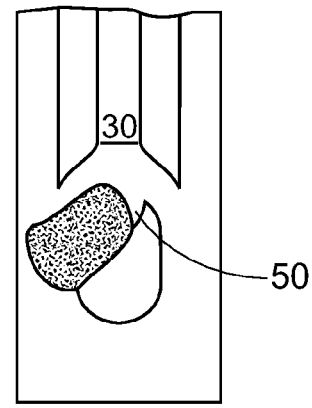
Figure 5C:
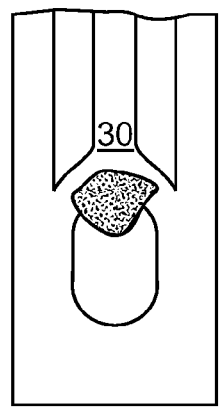
Figure 5D:
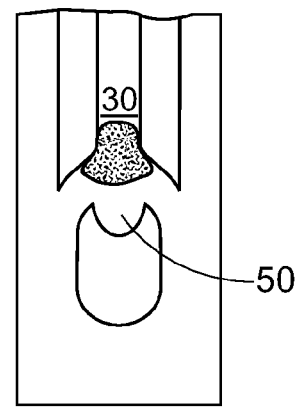

FIG. 5A, FIG. 5B, FIGS. 5C, and 5D which are arranged in a similar time-lapsed format, show how the droplet is centered on the strip and travels to the capillary channel. In FIG. 5A, a droplet is shown oriented on one side of the strip as the depending portion contacts the strip. In FIG. 5B, as the leading edge of the depending portion advances in the direction of travel A, the droplet is directed along the curved edge of the depending portion 50 toward the center of the strip. FIG. 5C shows the droplet moments later, centered and directed toward the mouth of the capillary channel.

In a preferred embodiment, the depending portion 50 is formed at the side of the lancet hole space. Slits 70 are cut into the strip, as shown in FIGS. 7A, 7B, 7C, 7D, and 7E so that depending portion is able to extend away at least about 100 μm from the plane of the strip when the strip bends, and preferably about 250 μm, or more. The curve or angle of the edge of the depending portion 50 guides the droplet toward the centerline of the strip where the mouth of the capillary channel is located. The slits 70 may have a length of about 1 mm to about 2 mm. The shape of slits 70 is not particularly limited, and the depending portion 50 may have a V shape, a U shape or any other convenient shape. Generally, it is preferred to have the shape of the depending portion narrow in the direction of the droplet. Thus, the slits 70 may form a crescent shape in some embodiments and a triangle in other embodiments. The curved slits in this embodiment are believed to assist in directing the droplet toward the center of the strip.

Figure 6:
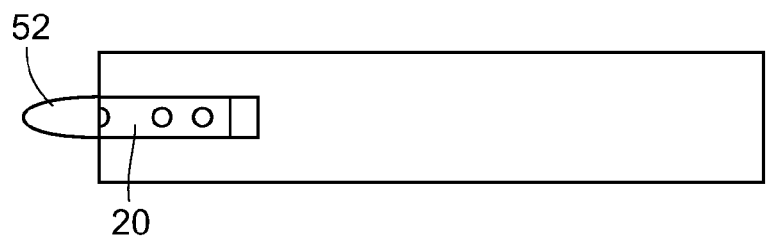
FIG. 6 depicts an alternative embodiment of a test strip according to the invention.
Figure 7A:
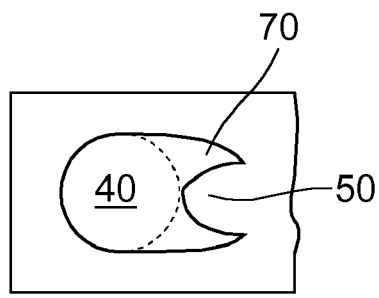
FIG. 7A, FIG. 7B, FIG. 7C, FIG. 7D, and FIG. 7E depict embodiments of the test strip according to the invention, where the depending portion has different shapes and configurations.
Figure 7B:
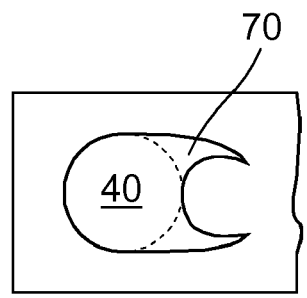
Figure 7C:
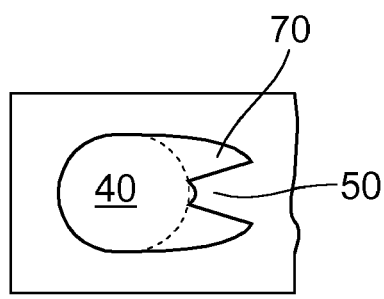
Figure 7D:
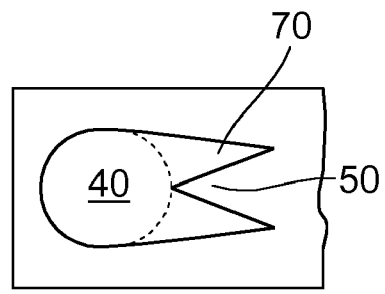
Figure 7E:
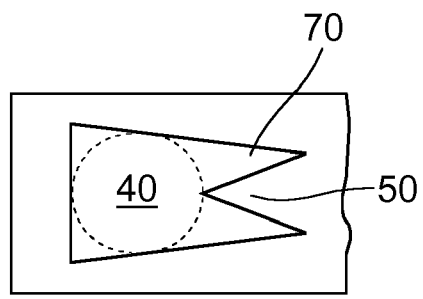

In an alternative embodiment, the depending portion may be placed on a strip as shown in FIG. 6. In FIG. 6, depending portion 52 extends from the side of an individual strip and contacts and guides the droplet to the capillary channel in a similar fashion to the previously described embodiments, in that initial contact of the blood sample is with a narrow part of the depending portion. In this embodiment, the channel 20 is on the side of the strip.

Without departing from the scope of the invention, test strips according to the invention may be embodied as several strip "units" on a continuous strip, so that a plurality of test sites can be located on a single strip and multiple test capability may be provided in a single device. Alternatively, single strips may be provided.

The foregoing description of the preferred embodiments is not to be deemed limiting of the invention, which is defined in the following claims.

What is claimed is:

1. A test strip for testing a fluid sample, comprising:
a strip with a first major side for positioning facing a the fluid sample;
a capillary channel having a mouth and having a measurement site;
a raised fluid transport path on the strip terminating at the mouth of the capillary channel;
a raised depending portion that is integral to the raised fluid transport path and positioned at an end of the raised fluid transport path opposite the mouth of the capillary channel, whereby a droplet of the fluid sample contacting the raised depending portion is directed to the raised fluid transport path; and
a lancet hole through the strip that is positioned laterally adjacent to the raised depending portion.

2. The test strip according to claim 1, wherein the raised depending portion is formed by two slits in the strip extending from the lancet hole in a direction toward the capillary channel.

3. The test strip according to claim 1, wherein the strip is bent, causing the raised depending portion to extend away from the first major side of the test strip by at least about 100 μm.

4. The test strip according to claim 1, wherein the lancet hole has a widest dimension of about 1 mm to about 2 mm.

5. The test strip according to claim 2, wherein the two slits have an approximately equal length of greater than about 1 mm forming the raised depending portion at the side of the lancet hole.

6. The test strip according to claim 1, wherein a portion of the strip is in a bent state, and moves along the strip during use in a direction opposite to the direction of fluid sample on the strip.

7. The test strip according to claim 1, wherein the measurement site comprises wells containing reagent for an electrochemical detection of glucose in a blood sample.

8. The test strip according to claim 1, wherein a surface of the capillary channel is hydrophilic.

9. The test strip according to claim 1, wherein a surface of the raised fluid transport path is hydrophobic.

10. The test strip according to claim 8, wherein the surface of the capillary channel has sufficient hydrophilicity so that a droplet of blood thereon forms a contact angle of less than about 50 degrees.

11. The test strip according to claim 9, wherein the surface of the raised fluid transport path has sufficient hydrophobicity so that a droplet of blood thereon forms a contact angle of greater than about 50 degrees.

12. The test strip according to claim 1, comprising a plurality of patterned polymeric structural layers that are configured to form when successively stacked the strip, the raised fluid transport path and integral raised depending portion, and the capillary channel.

13. The test strip according to claim 1, wherein the volume of the capillary channel is less than about 1.0 μL.

14. The test strip according to claim 1, further comprising two recesses respectively adjacent to each lateral side of the raised fluid transport path, each recess extending substantially the entire length of the raised fluid transport path, from near the raised depending portion to near the mouth of the capillary channel.

15. A test strip for testing a fluid sample, comprising:
a strip with a first major side for positioning the fluid sample;
a capillary channel having a mouth and having a measurement site;
a raised fluid transport path on the strip having sides and an end at the mouth of the capillary channel;
at least one recess adjacent a side of the raised fluid transport path, whereby the fluid sample contacting the raised fluid transport path is preferentially directed to the mouth of the capillary channel; and
a lancet hole through the strip that is positioned adjacent to a raised depending portion, the raised depending portion being integral to the raised fluid transport path and positioned at an end of the raised fluid transport path opposite the mouth of the capillary channel.

16. The test strip according to claim 15, wherein the at least one recess comprises two recesses respectively positioned on opposite sides of the raised fluid transport path, such that the raised fluid transport path has a width narrower than the lancet hole at its widest point.

* * * * *